United States Patent
Saarinen

(10) Patent No.: US 11,630,028 B2
(45) Date of Patent: Apr. 18, 2023

(54) METHOD AND CONTROLLER FOR DECIDING WHETHER A BEARING IS FAULTY OR NOT

(71) Applicant: ABB Schweiz AG, Baden (CH)

(72) Inventor: Kari Saarinen, Västerås (SE)

(73) Assignee: ABB Schweiz AG, Baden (CH)

(*) Notice: Subject to any disclaimer, the term of this patent is extended or adjusted under 35 U.S.C. 154(b) by 179 days.

(21) Appl. No.: 17/254,348

(22) PCT Filed: Jun. 25, 2019

(86) PCT No.: PCT/EP2019/066880
§ 371 (c)(1),
(2) Date: Dec. 21, 2020

(87) PCT Pub. No.: WO2020/002356
PCT Pub. Date: Jan. 2, 2020

(65) Prior Publication Data
US 2021/0262894 A1    Aug. 26, 2021

(30) Foreign Application Priority Data
Jun. 27, 2018   (EP) .................................... 18180093

(51) Int. Cl.
*G01M 13/04*    (2019.01)
*G01N 33/28*    (2006.01)

(52) U.S. Cl.
CPC ........ *G01M 13/04* (2013.01); *G01N 33/2858* (2013.01)

(58) Field of Classification Search
CPC ........................... G01M 13/04; G01N 33/2858
See application file for complete search history.

(56) References Cited

U.S. PATENT DOCUMENTS

| | | | | |
|---|---|---|---|---|
| 4,528,852 A | * | 7/1985 | Sohoel | ..................... F16N 29/00 340/682 |
| 2001/0030466 A1 | * | 10/2001 | Ehrlich | ................... F16C 19/52 303/191 |

(Continued)

FOREIGN PATENT DOCUMENTS

| EP | 2365310 A1 | 9/2011 |
|---|---|---|
| EP | 3242118 A1 | 11/2017 |

OTHER PUBLICATIONS

International Search Report and Written Opinion of the International Searching Authority; Application No. PCT/EP2019/066880; Completed: Aug. 16, 2019; dated Aug. 28, 2019; 14 pages.

*Primary Examiner* — Eric S. McCall
(74) *Attorney, Agent, or Firm* — Whitmyer IP Group LLC

(57) ABSTRACT

There is provided mechanisms for deciding whether a bearing is faulty or not. A method is performed by a controller. The method comprises obtaining, as a measurement signal, metal particles counting data, where the metal particles counting data indicates number of metal particles present in lubrication oil of the bearing per time unit. The method comprises differentiating the measurement signal, resulting in a differentiated measurement signal. The method comprises deciding, depending on how large share of a probability density estimate of the differentiated measurement signal is above a threshold value, whether the bearing is faulty or not.

16 Claims, 7 Drawing Sheets

(56) References Cited

U.S. PATENT DOCUMENTS

| | | | |
|---|---|---|---|
| 2002/0083779 A1* | 7/2002 | Narita | G01M 13/045 73/862.191 |
| 2002/0105429 A1* | 8/2002 | Donner | B61K 9/04 340/682 |
| 2003/0066352 A1* | 4/2003 | Leamy | F01D 21/00 73/659 |
| 2003/0098691 A1* | 5/2003 | Matsuyama | F16C 33/6674 324/525 |
| 2007/0277613 A1* | 12/2007 | Iwatsubo | G01M 13/045 702/141 |
| 2011/0040495 A1* | 2/2011 | El-Refaie | G01M 13/04 702/182 |
| 2012/0067111 A1* | 3/2012 | Lindner | F16C 17/24 73/53.05 |
| 2017/0058956 A1* | 3/2017 | Dittes | F16C 19/52 |
| 2019/0226944 A1* | 7/2019 | Saarinen | G01M 13/04 |
| 2021/0025781 A1* | 1/2021 | Saarinen | G01M 13/045 |
| 2022/0050017 A1* | 2/2022 | Saarinen | G06F 30/17 |

* cited by examiner

METHOD AND CONTROLLER FOR DECIDING WHETHER A BEARING IS FAULTY OR NOT

TECHNICAL FIELD

Embodiments presented herein relate to a method, a controller, a computer program, and a computer program product for deciding whether a bearing is faulty or not.

BACKGROUND

In general terms, a rolling-element bearing (REB), also known as a rolling bearing, is a bearing which carries a load by placing rolling elements (such as balls or rollers) between two bearing rings called races. The relative motion of the races cause the rolling elements to roll with very little rolling resistance and with little sliding.

In general terms, REBs are common elements in various rotating machines and the failure of bearing is a common reason for machine breakdowns. Economical losses due to an unexpected failure of a critical bearing can be significantly reduced by applying a proper maintenance strategy. When using condition based maintenance it could be possible to detect incipient faults so early that it is possible to perform maintenance actions before the bearing fails. Early fault detection could be even more important in applications where there are planned maintenance breaks at regular intervals since the probability that the REB can be replaced without any additional stoppages increases with earlier detection.

At relatively early failure stage, a faulty bearing generally starts to generate metallic debris, which can be detected by using an oil debris monitoring system, either based on regularly taken oil samples analyzed in a laboratory (so-called off-line analysis), or based on oil debris sensors configured to detect metal particles on-line.

Based on the measurement results (obtained either off-line or on-line) a service technician, or engineer, should make a decision whether the bearing is damaged, i.e., faulty, or not. In practice, the analysis is mostly performed manually; a service technician observes trends of total counts of metal particles, or total weight of measured metal particles, together with pre-defined alarm limits, where alarm limits are defined for the amount of weekly or monthly generated metal particles. Due to disturbances, for example sudden large changes in particle counts, which origin is not a bearing fault, early fault detection based on metal particles is difficult.

Reference is here made to FIG. 1 and FIG. 2, both indicating the number of detected iron (Fe) particles in the lubrication oil of a bearing at an electric podded azimuth thruster (AZIPOD®). In FIG. 1 there are several step-changes in metals particles counts. However, a bearing fault only occurred after a number of such step-changes. A similar type of large step-changes in metals particles counts is also clearly visible in FIG. 2. However, in this case no bearing fault occurs during the observation period. For example, due to the similarities between the curves in FIGS. 1 and 2, the likelihood of either a false alarm (i.e., interpreting the behavior of the curve in FIG. 2 as indicating a faulty bearing), or detecting the faulty bearing too late or not at all (as might be the case for the curve in FIG. 1) is high.

Hence, there is a need for improved detection of faulty bearings.

SUMMARY

An object of embodiments herein is to provide efficient detection of faulty bearings not suffering from the issues noted above, or at least where these issues are mitigated or reduced.

According to a first aspect there is presented a method for deciding whether a bearing is faulty or not. The method is performed by a controller. The method comprises obtaining, as a measurement signal, metal particles counting data, where the metal particles counting data indicates number of metal particles present in lubrication oil of the bearing per time unit. The method comprises differentiating the measurement signal, resulting in a differentiated measurement signal. The method comprises deciding, depending on how large share of a probability density estimate of the differentiated measurement signal is above a threshold value, whether the bearing is faulty or not.

According to a second aspect there is presented a controller for deciding whether a bearing is faulty or not. The controller comprises processing circuitry. The processing circuitry is configured to cause the controller to obtain, as a measurement signal, metal particles counting data, where the metal particles counting data indicates number of metal particles present in lubrication oil of the bearing per time unit. The processing circuitry is configured to cause the controller to differentiate the measurement signal, resulting in a differentiated measurement signal. The processing circuitry is configured to cause the controller to decide, depending on how large share of a probability density estimate of the differentiated measurement signal is above a threshold value, whether the bearing is faulty or not.

According to a third aspect there is presented a controller for deciding whether a bearing is faulty or not. The controller comprises an obtain module configured to obtain, as a measurement signal, metal particles counting data, where the metal particles counting data indicates number of metal particles present in lubrication oil of the bearing per time unit. The controller comprises a differentiate module configured to differentiate the measurement signal, resulting in a differentiated measurement signal. The controller comprises a decide module configured to decide, depending on how large share of a probability density estimate of the differentiated measurement signal is above a threshold value, whether the bearing is faulty or not.

Advantageously this method and this controller provide efficient detection of faulty bearings.

Advantageously the disclosed detection of faulty bearings does not suffer from the issues noted above.

Advantageously this method and this controller are able to detect the bearing fault even three months earlier than when using traditional fault detection methods.

Advantageously this method and this controller are able to detect bearing faults that cannot be detected using traditional fault detection methods.

Advantageously, due to early fault detection, also the actions to prolong the remaining useful life of the bearing can be started earlier, which results in longer life and smaller effects on operation conditions.

According to a fourth aspect there is presented a computer program for deciding whether a bearing is faulty or not, the computer program comprising computer program code which, when run on a controller, causes the controller to perform a method according to the first aspect.

According to a fifth aspect there is presented a computer program product comprising a computer program according to the fourth aspect and a computer readable storage medium on which the computer program is stored. The computer readable storage medium could be a non-transitory computer readable storage medium.

It is to be noted that any feature of the first, second, third, fourth, and fifth aspects may be applied to any other aspect, wherever appropriate. Likewise, any advantage of the first aspect may equally apply to the second, third, fourth, and/or fifth aspect, respectively, and vice versa. Other objectives, features and advantages of the enclosed embodiments will be apparent from the following detailed disclosure, from the attached dependent claims as well as from the drawings.

Generally, all terms used in the claims are to be interpreted according to their ordinary meaning in the technical field, unless explicitly defined otherwise herein. All references to "a/an/the element, apparatus, component, means, module, step, etc." are to be interpreted openly as referring to at least one instance of the element, apparatus, component, means, module, step, etc., unless explicitly stated otherwise. The steps of any method disclosed herein do not have to be performed in the exact order disclosed, unless explicitly stated.

BRIEF DESCRIPTION OF THE DRAWINGS

The inventive concept is now described, by way of example, with reference to the accompanying drawings, in which.

DETAILED DESCRIPTION

The inventive concept will now be described more fully hereinafter with reference to the accompanying drawings, in which certain embodiments of the inventive concept are shown. This inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description. Any step or feature illustrated by dashed lines should be regarded as optional.

Figure 1:
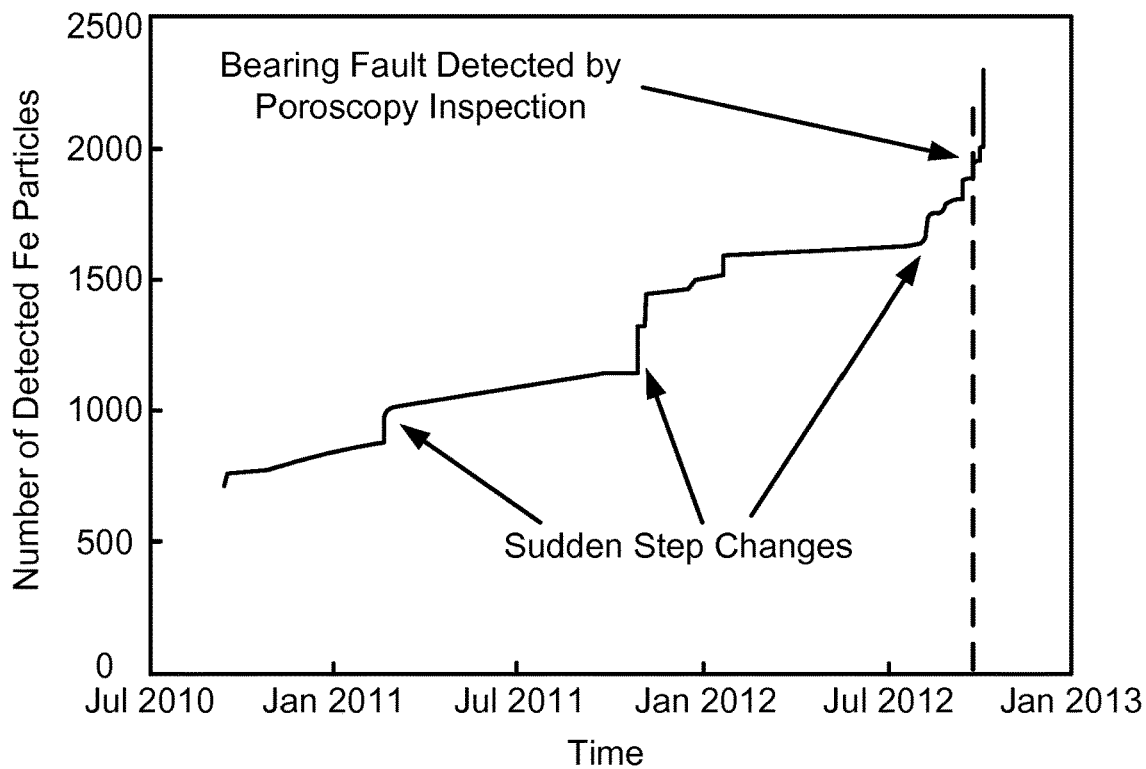
FIGS. 1 and 2 are examples of number of detected iron particles in lubrication oil as a function of time.
Figure 2:
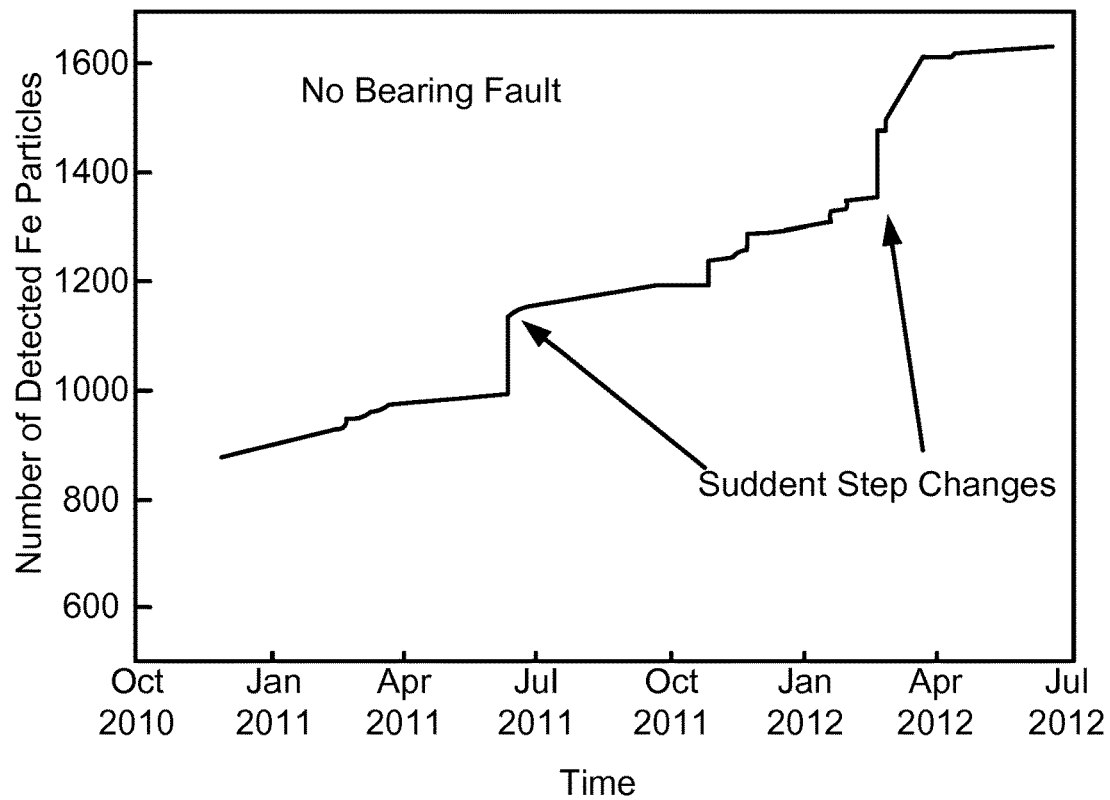
Figure 3:
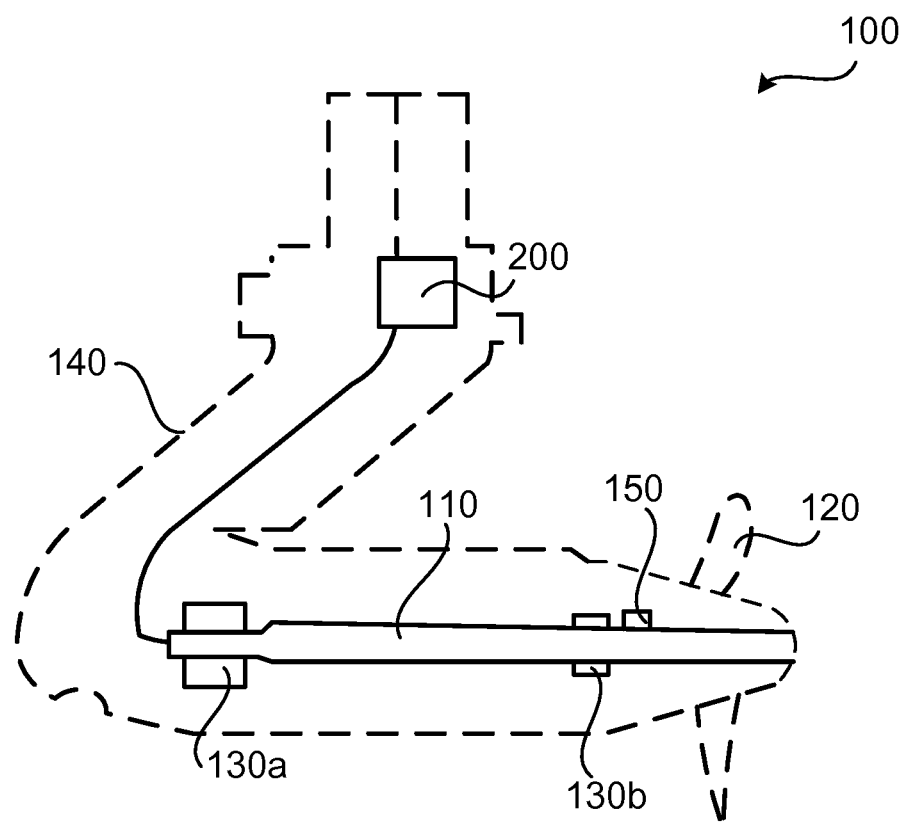
FIG. 3 schematically illustrates bearings provided in an azimuth thruster according to an embodiment.

FIG. 3 is a schematic illustration of an azimuth thruster 100 according to an embodiment. The azimuth thruster 100 is an electric podded azimuth thruster (AZIPOD®) 100 and comprises a propeller shaft 110 on which propeller blades 120 are provided. The propeller shaft 110 is supported by at least one bearing 130a, 130b. The interior of the azimuth thruster 100 is enclosed by a water-tight casing, or hull, 140.

A controller 200 is provided for deciding whether a bearing 130a, 130b is faulty or not and is therefore configured to, from sensors 150, obtain a measurement signal of metal particles counting data present in the lubrication oil of the bearing 130a, 130b.

The embodiments disclosed herein relate to mechanisms for deciding whether a bearing 130a, 130b is faulty or not. In order to obtain such mechanisms there is provided a controller 200, a method performed by the controller 200, a computer program product comprising code, for example in the form of a computer program, that when run on a controller 200, causes the controller 200 to perform the method.

In further detail, at least some of the embodiments disclosed herein are based on realizing that the probability density function of the differentiated measurement signal is different for the case of healthy bearing 130a, 130b compared to the case of an incipient fault of the bearing 130a, 130b.

Figure 4:
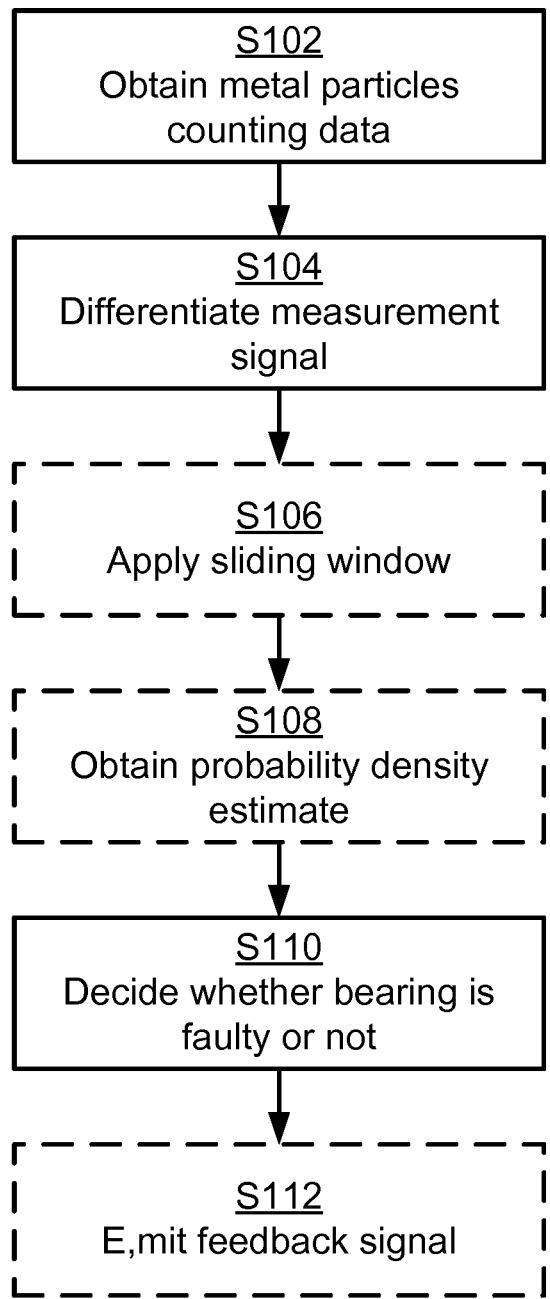
FIG. 4 is a flowchart of methods according to embodiments.

FIG. 4 is a flowchart illustrating embodiments of methods for deciding whether a bearing 130a, 130b is faulty or not. The methods are performed by the controller 200. The methods are advantageously provided as computer programs 920.

S102: The controller 200 obtains, as a measurement signal, metal particles counting data. The metal particles counting data indicates the number of metal particles present in the lubrication oil of the bearing 130a, 130b per time unit. In this respect there is thus one sample of the measurement signal (and thus one sample of the metal particles counting data) per time unit.

S104: The controller 200 differentiates the measurement signal, resulting in a differentiated measurement signal. Examples of how the measurement signal might be differentiated will be disclosed below.

S110: The controller 200 decides, depending on how large share of a probability density estimate of the differentiated measurement signal is above a threshold value, whether the bearing 130a, 130b is faulty or not.

Embodiments relating to further details of deciding whether a bearing 130a, 130b is faulty or not as performed by the controller 200 will now be disclosed.

In some aspect a feedback signal is emitted upon the bearing 130a, 130b having been decided to be faulty. Particularly, according to an embodiment the controller 200 is configured to perform (optional) step S112:

S112: The controller 200, upon having decided the bearing 130a, 130b as faulty, emits a feedback signal. The feedback signal is indicative of the bearing 130a, 130b being decided as faulty.

In some aspects the feedback signal is an alarm system and is sent towards a user interface.

In some aspects the feedback signal is a control system and is sent towards a controller, or engine, of the propeller shaft no. The controller, or engine, might then be configured to act accordingly, e.g. reducing the speed of the propeller shaft no once it has received the feedback signal that the bearing 130a, 130b is decided as faulty.

In some aspects a feedback signal is emitted even when the bearing 130a, 130b is not decided to be faulty. This feedback signal is then not indicative of the bearing 130a, 130b being decided as faulty.

There could be different ways to differentiate the measurement signal. Let sample k of the measurement signal be represented by Fe[k], where k=1, 2, ..., K, and where K thus is the total number of samples in the measurement signal received so far; as more samples are received the value of K will thus increase. Further, let sample k of the differentiated measurement signal be represented by dFe[k]. Then, according to an embodiment, dFe[k] is given by:

$$dFe[k]=(Fe[k+1]-Fe[k])/(t[k+1]-t[k]), \text{ for } k=1,2,\ldots,K-1,$$

where t[k] represents the point in time for sample k.

Various alternative ways to differentiate the measurement signal can be applied. Some examples are found in "Handbook of Mathematical Functions", Dover, 1968, by M. Abramovitz and I. Stegun. Differentiation of the measurement signal can be made also by using finite input response (FIR)-type of filters, see for example "Discrete-time Signal Processing", Prentice Hall, 1989, by A. V. Oppenheimer and R. W. Schafer.

In some aspects a sliding window is applied to the the differentiated measurement signal before the probability density estimate of the differentiated measurement signal is obtained. Particularly, according to an embodiment the controller 200 is configured to perform (optional) step S106:

S106: The controller 200 applies a sliding window to the differentiated measurement signal, resulting in vectors of windowed differentiated measurement signals.

Assuming that the sliding window has length N, one such vector $v^K=[v[K-N+1], \ldots, v[N]]$ thus comprises the N recent-most values of dFe[k]. That is, $$v^K=[dFe[K-N+1],dFe[K-N+2],\ldots,dFe[K]].$$

Another way to represent the vector $v^K$ where L is the length of the window is:

$$v^K=[dFe[K],dFe[K-1],\ldots,dFe[K-L+1]].$$

In some aspects one probability density estimate is made for each such vector of windowed differentiated measurement signals. Particularly, according to an embodiment the controller 200 is configured to perform (optional) step S108:

S108: The controller 200 obtains one probability density estimate of the differentiated measurement signal per vector of the of windowed differentiated measurement signal.

The deciding in step S110 is then performed for each probability density estimate such that one decision whether the bearing 130a, 130b is faulty or not is made per each probability density estimate.

There could be different ways for the controller 200 to obtain the probability density estimate of the differentiated measurement signal. In some aspects the probability density estimate is estimated by a (normalized) histogram. That is, according to an embodiment, the probability density estimate of the differentiated measurement signal is represented by a histogram of the differentiated measurement signal. The relative share of values can thus e.g. be described using density functions or normalized histograms.

Denote by $f_K(dFe)$ the probability density estimate. A value of the distribution that represents the relative share of differentials which values are larger than a pre-defined limit $B_1$, which thus defines the threshold value, can be used as a characteristic x(K). That is:

$$x(K) = Pr(dFe > B_1) = \int_{B_1}^{\infty} f_K(dFe)d(dFe) = 1 - \int_0^{B_1} f_K(dFe)d(dFe)$$

A statistical binary decision method can then be applied to the characteristics x(K) to decide if the bearing is faulty or not. If a histogram is used, the characteristics is represented by x[K] to indicate that the characteristics is discrete valued.

That is, the characteristics (either x(K) or x[K]) represents the share of the probability density estimate of the differentiated measurement signal that is above the threshold value.

If the threshold value $B_1$ is located close to, or on, the boundary between the first and the second bin, and the number of differentials in the sliding window that are smaller than this threshold is denoted by $N_1$, then the characteristics can be determined as:

$$x[K] = 1 - \frac{N_1}{L},$$

where K is the number of the last sample collected so far and L is the length of the sliding window (i.e., there are L samples within the sliding window). A statistical binary decision method can then be applied to the characteristics x[K] to decide if the bearing is faulty or not.

In view of the above, when the bearing is healthy most of the differentials are zero or close to zero except when there are stepwise disturbances in the signal. However, the number of the stepwise changes is small during e.g. a week compared to the total number measured values during the same period. Therefore, the relative share of large differentials due disturbances is quite low. Whereas when there is a fault in a bearing the relative share of the non-zero differentials is larger. The relative share of values can be described using density functions (resulting in characteristic x(K)) or normalized histograms (resulting in characteristic x[K]).

There could be different ways to determine what share of the probability density estimate of the differentiated measurement signal to compare to the threshold value.

In some aspects this share is found as 1−r, where the value of r is given by the relative share of differentials belonging to the first bin of the histogram. That is, according to an embodiment the share of the probability density estimate of the differentiated measurement signal to compare to the threshold value is defined by 1−r, where r has a value given by the relative number of values of the differentiated measurement signal belonging to a lowest-most bin of the histogram. Thus, r takes a value in the interval [0, 1].

According to a further embodiment, the histogram at least comprises a first bin representing the smallest differentiated measurement signal and a last bin representing the largest differentiated measurement signal. The share of the probability density estimate of the differentiated measurement signal to compare to the threshold value is then defined by that share of the differentiated measurement signal located in all but the first bin. According to a yet further embodiment the histogram further comprises at least one middle bin, where each at least one middle bin represents an increasing differentiated measurement signal between the smallest differentiated measurement signal and the largest smallest differentiated measurement signal. The share of the probability density estimate of the differentiated measurement signal to compare to the threshold value might then be defined by that share of the differentiated measurement signal located in all but the first bin. Further, if there are at least four bins, the share of the probability density estimate of the differentiated measurement signal to compare to the threshold value might then be defined by that share of the differentiated measurement signal located in all but the first two bins. Further, if there are at least ten bins, the share of the probability density estimate of the differentiated measurement signal to compare to the threshold value might then be defined by that share of the differentiated measurement signal located in all but the first three bins, or all but the first four bins.

There could be different ways to set the threshold value as used in step S110 when deciding whether the bearing 130a, 130b is faulty or not. According to an embodiment, the threshold value is set to between 10 and 100 in units of metal particles per day. That is, according to an embodiment, the threshold value corresponds to between 10 and 100 metal particles per day, preferably between 20 and 50 metal particles per day. In further aspects, when the probability density estimate of the differentiated measurement signal is represented by a histogram of the differentiated measurement signal the threshold value might be set depending on how many bins of the differentiated measurement signal are used for comparison to the threshold value. That is, according to an illustrative example, if the share of the differentiated measurement signal located in all but the first bin amounts to at least 20 to 50 particles per day, the bearing 130a, 130b is decided to be faulty.

Figure 5:
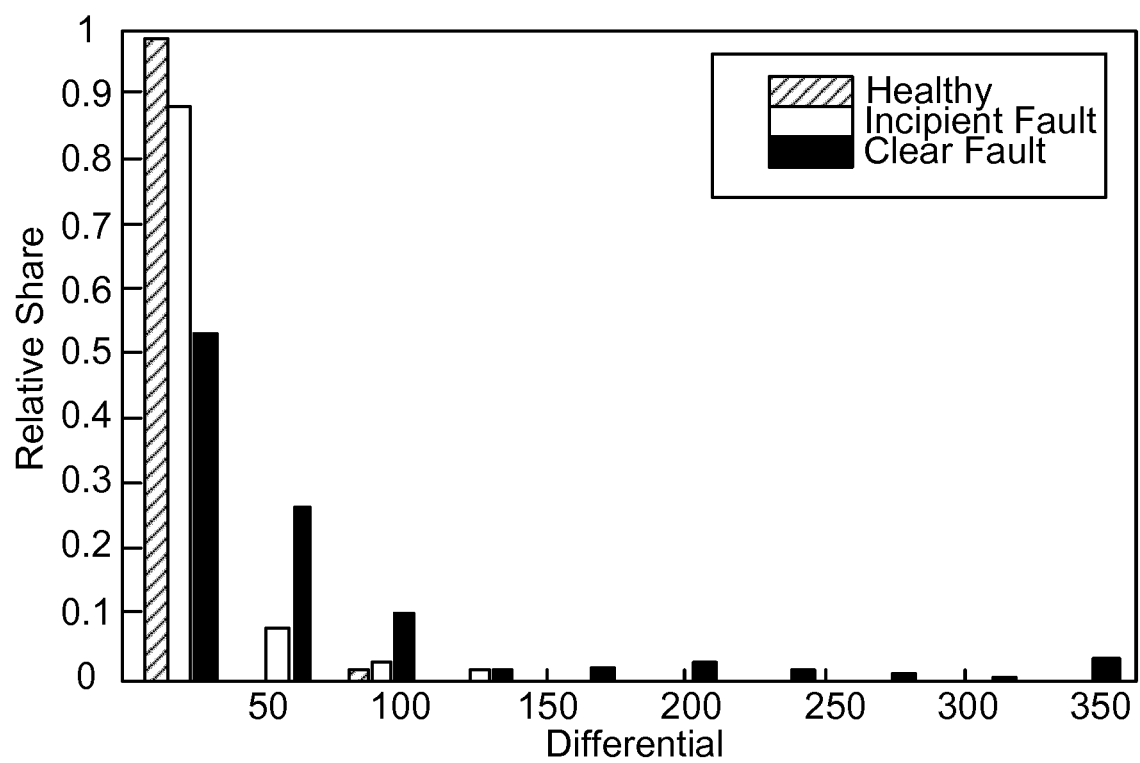
FIG. 5 is a histogram of differentiated measurement signals according to embodiments.

FIG. 5 shows an example of probability density estimate of a differentiated measurement signal, where the probability density estimate is represented by a normalized histogram having 10 bins of uniform length for values ranging from 0 to 360. That is, the first bin represents values of a differentiated measurement signal corresponding to between 0 and 36 metal particles per day; the second bin represents between 37 and 72 metal particles per day, and so on. FIG. 5 further shows the histograms for three representative cases; a first case of a healthy bearing, a second case of a bearing with an incipient fault, and a third case of a faulty bearing. Using the above notation, when the bearing is healthy almost all differentials are zeros which means that $N_1$ is almost the same as L, and the characteristics x[K] is close to zero.

As shown in FIG. 5, the share of the differentiated measurement signal for the healthy bearing in the first bin is more than 0.95; only a very small share is present in the third bin. For the bearing with an incipient fault the share of the differentiated measurement signal in the first bin is about 0.87 and the remaining share is spread between the second, third, and fourth bins. For the faulty bearing the share in the first bin is only about 0.55 and the remaining share is spread between all remaining bins. Hence, a larger share of the differentiated measurement signal is located outside the first bin for the bearing with an incipient fault compared to the healthy bearing, and a larger share of the differentiated measurement signal is located outside the first bin for the faulty bearing compared to the bearing with an incipient fault.

There could be different ways to in step S110 decide whether the bearing 130a, 130b is faulty or not. According to an embodiment the deciding in step S110 is based on applying a statistical binary decision method to a parameter defined by the share of a probability density estimate of the differentiated measurement signal being above the threshold value $B_1$. One examples of such a parameter is the characteristics, given by either x(K) or x[K].

Examples of statistical binary decision methods include, but are not limited to, moving average control chart, cumulative sum algorithm and repeated sequential probability ratio test, see "Detection of Abrupt Changes: Theory and Application", Prentice-Hall, 1993, by M. Basseville, I. V. Nikiforov.

There could be different units of time where a new sample of the metal particles counting data is obtained. For example, a new sample could be obtained once every hour, once every day, or once every week. That is, according to an embodiment, the time unit is one hour, one day, or one week.

There could be different types of bearings 130a, 130b. According to an embodiment the bearing 130a, 130b is a rolling-element bearing. With reference to the illustrative example of FIG. 3, the bearing 130a, 130b could be part of an electric podded azimuth thruster (AZIPODC)) 100.

Figure 6:
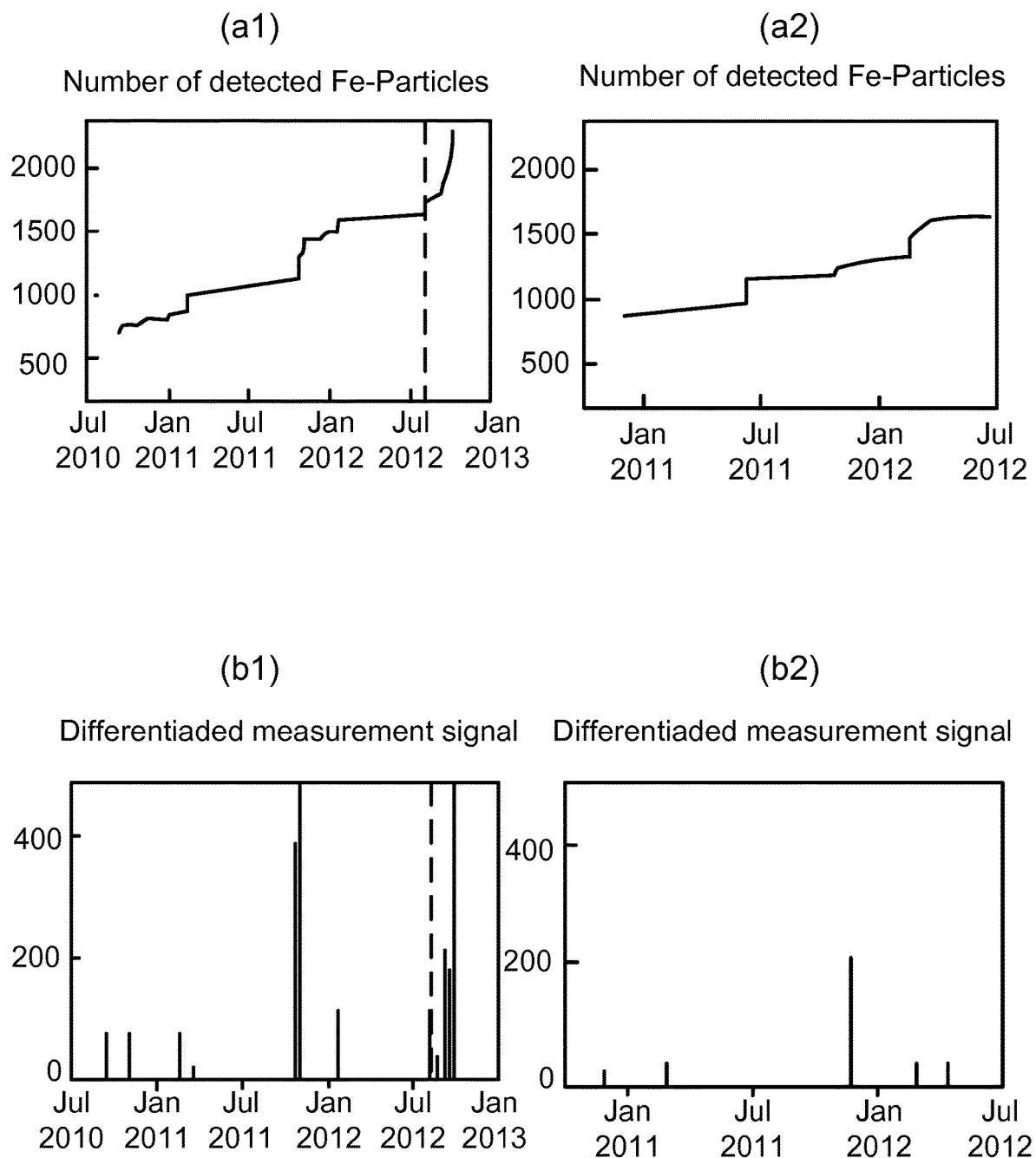
FIG. 6 schematically illustrates measurement signals resulting from different execution steps according to embodiments.
Figure 6:
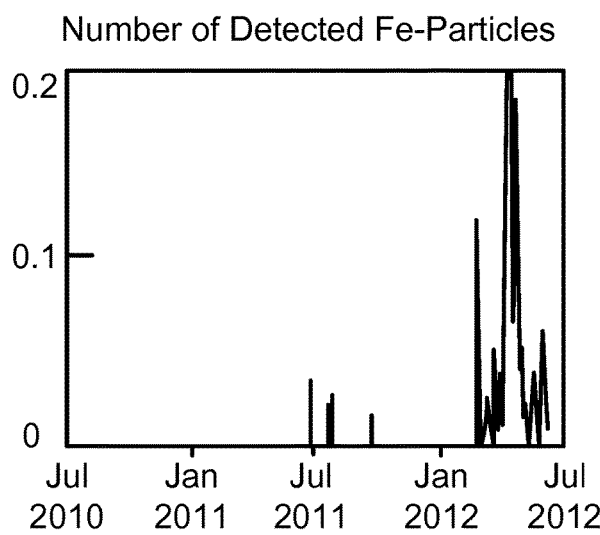
Figure 6:
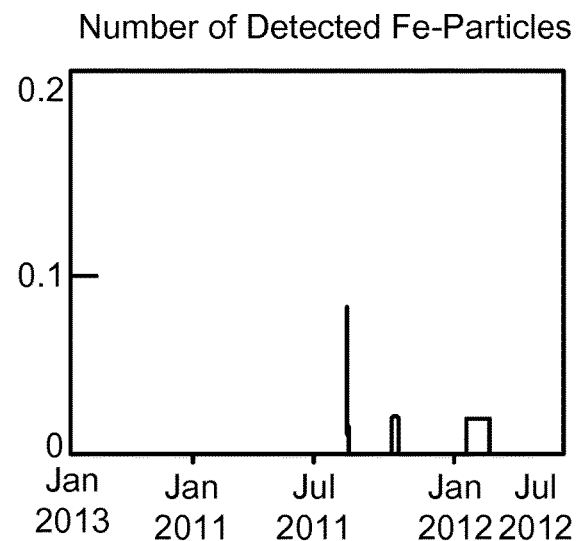
Figure 6:
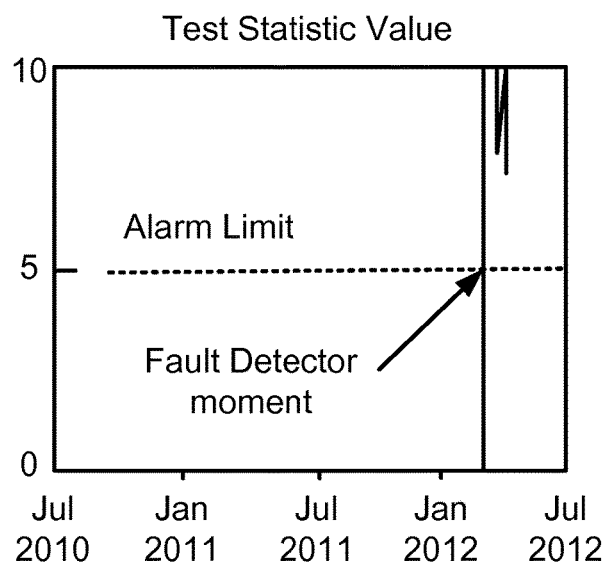
Figure 6:
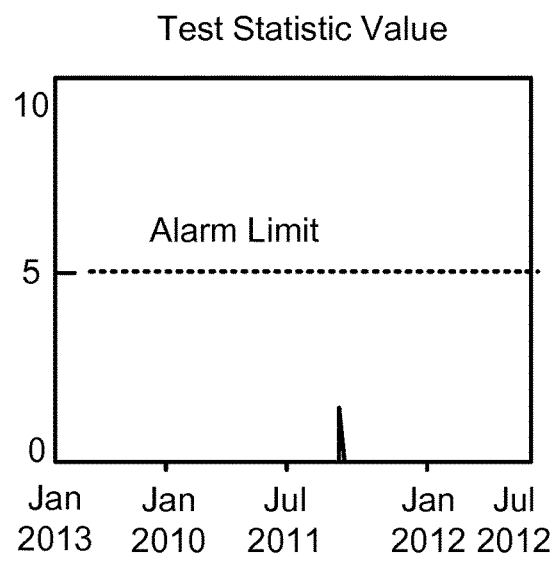

FIG. 6 shows the measurement signal after executing each respective step of the method. The measurement signal represents metal particles counting data for iron particles collected from a sensor 150 for two cases; a healthy bearing 130a, 130b of an electric podded azimuth thruster 100 (FIG. 6 at (a1), (b1), (c1), (d1)) and a faulty bearing 130a, 130b of an electric podded azimuth thruster 100 (FIG. 6 at (a2), (b2), (c2), (d2)).

The length of the sliding window was set to one week. The probability density estimates were represented by normalized histograms having 10 bins of uniform length for values ranging from 0 to 360. The relative share of the differentiated measurement signal belonging to all but the first bin was used when comparing to the threshold value. A common cumulative sum algorithm was used to calculate test statistics for decision making with a decision limit set to 5. At (a) is shown the number of detected iron particles as a function of time. At (b) is shown the differentiated measurement signal as a function of time. At (c) is shown the share of a probability density estimate of the differentiated measurement signal in all but the first bin. At (d) is shown the test statistics.

Figure 7:
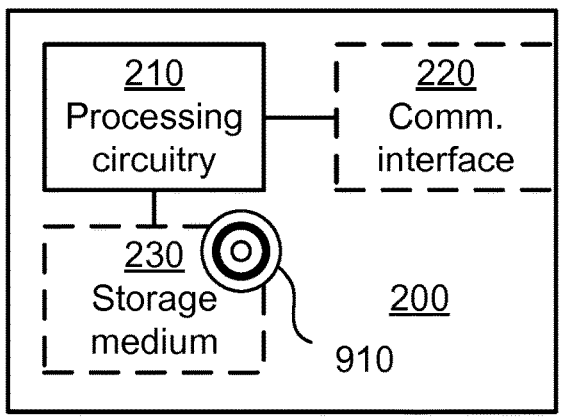
FIG. 7 is a schematic diagram showing functional units of a controller according to an embodiment.

FIG. 7 schematically illustrates, in terms of a number of functional units, the components of a controller 200 according to an embodiment. Processing circuitry 210 is provided using any combination of one or more of a suitable central processing unit (CPU), multiprocessor, microcontroller, digital signal processor (DSP), etc., capable of executing software instructions stored in a computer program product 910 (as in FIG. 9), e.g. in the form of a storage medium 230. The processing circuitry 210 may further be provided as at least one application specific integrated circuit (ASIC), or field programmable gate array (FPGA).

Particularly, the processing circuitry 210 is configured to cause the controller 200 to perform a set of operations, or steps, S102-S106, as disclosed above. For example, the storage medium 230 may store the set of operations, and the processing circuitry 210 may be configured to retrieve the set of operations from the storage medium 230 to cause the controller 200 to perform the set of operations. The set of operations may be provided as a set of executable instructions.

Thus the processing circuitry 210 is thereby arranged to execute methods as herein disclosed. The storage medium 230 may also comprise persistent storage, which, for example, can be any single one or combination of magnetic memory, optical memory, solid state memory or even remotely mounted memory. The controller 200 may further comprise a communications interface 220 at least configured for communications with sensors 150, such as sensors 150 of an azimuth thruster 100, and to emit feedback to a user interface. As such the communications interface 220 may comprise one or more transmitters and receivers, comprising analogue and digital components.

The processing circuitry 210 controls the general operation of the controller 200 e.g. by sending data and control signals to the communications interface 220 and the storage medium 230, by receiving data and reports from the communications interface 220, and by retrieving data and instructions from the storage medium 23o. Other components, as well as the related functionality, of the controller 200 are omitted in order not to obscure the concepts presented herein.

Figure 8:
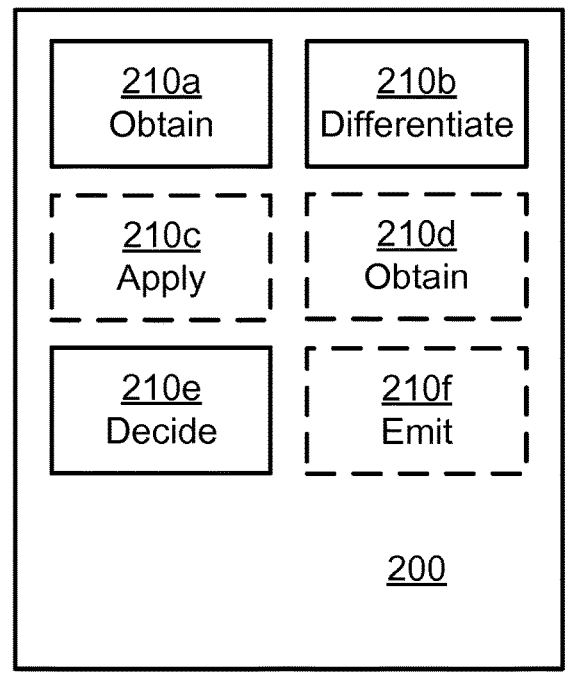
FIG. 8 is a schematic diagram showing functional modules of a controller according to an embodiment.

FIG. 8 schematically illustrates, in terms of a number of functional modules, the components of a controller 200 according to an embodiment. The controller 200 of FIG. 8 comprises a number of functional modules; an obtain module 210a configured to perform step S102, a differentiate module 210b configured to perform step S104, and a decide module 210e configured to perform step S110. The controller 200 of FIG. 8 may further comprise a number of optional functional modules, such as an apply module 210C configured to perform step S106, an obtain module 210d configured to perform step S108, and an emit module configured to perform step S112. In general terms, each functional module 210a-210f may in one embodiment be implemented only in hardware and in another embodiment with the help of software, i.e., the latter embodiment having computer program instructions stored on the storage medium 230 which when run on the processing circuitry makes the controller 200 perform the corresponding steps mentioned above in conjunction with FIG. 8. It should also be mentioned that even though the modules correspond to parts of a computer program, they do not need to be separate modules therein, but the way in which they are implemented in software is dependent on the programming language used. Preferably, one or more or all functional modules 210a-210f may be implemented by the processing circuitry 210, possibly in cooperation with the communications interface 220 and/or the storage medium 230. The processing circuitry 210 may thus be configured to from the storage medium 230 fetch instructions as provided by a functional module 210a-210f and to execute these instructions, thereby performing any steps as disclosed herein.

The controller 200 may be provided as a standalone device or as a part of at least one further device. For example, the controller 200 may be provided in the azimuth thruster 100. A first portion of the instructions performed by the controller 200 may be executed in a first device, and a second portion of the of the instructions performed by the controller 200 may be executed in a second device; the herein disclosed embodiments are not limited to any particular number of devices on which the instructions performed by the controller 200 may be executed. Hence, the methods according to the herein disclosed embodiments are suitable to be performed by a controller 200 residing in a cloud computational environment. Therefore, although a single processing circuitry 210 is illustrated in FIG. 7 the processing circuitry 210 may be distributed among a plurality of devices, or nodes. The same applies to the functional modules 210a-210f of FIG. 8 and the computer program 920 of FIG. 9 (see below).

Figure 9:
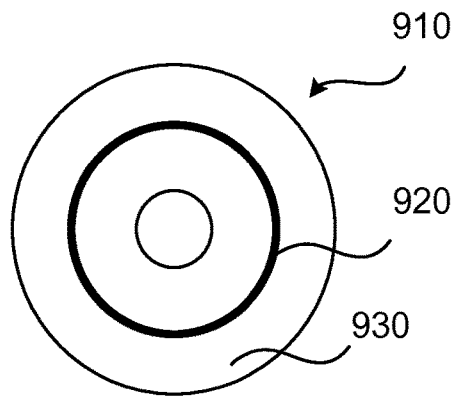
FIG. 9 shows one example of a computer program product comprising computer readable storage medium according to an embodiment.

FIG. 9 shows one example of a computer program product 910 comprising computer readable storage medium 930. On this computer readable storage medium 930, a computer program 920 can be stored, which computer program 920 can cause the processing circuitry 210 and thereto operatively coupled entities and devices, such as the communications interface 220 and the storage medium 230, to execute methods according to embodiments described herein. The computer program 920 and/or computer program product 910 may thus provide means for performing any steps as herein disclosed.

In the example of FIG. 9, the computer program product 910 is illustrated as an optical disc, such as a CD (compact disc) or a DVD (digital versatile disc) or a Blu-Ray disc. The computer program product 910 could also be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory. Thus, while the computer program 920 is here schematically shown as a track on the depicted optical disk, the computer program 920 can be stored in any way which is suitable for the computer program product 910.

The inventive concept has mainly been described above with reference to a few embodiments. However, as is readily appreciated by a person skilled in the art, other embodiments than the ones disclosed above are equally possible within the scope of the inventive concept, as defined by the appended patent claims.

The invention claimed is:

1. A computer program for deciding whether a bearing is faulty or not, the computer program comprising computer code which, when run on processing circuitry of a controller, causes the controller to:
   obtain, as a measurement signal, metal particles counting data, where the metal particles counting data indicates number of metal particles present in lubrication oil of the bearing per time unit;
   differentiate the measurement signal, resulting in a differentiated measurement signal; and
   decide, depending on how large share of a probability density estimate of the differentiated measurement signal is above a threshold value, whether the bearing is faulty or not, wherein the probability density estimate of the differentiated measurement signal is represented by a histogram of the differentiated measurement signal.

2. A computer program product comprising a computer program according to claim 1, and a computer readable storage medium on which the computer program is stored.

3. A controller for deciding whether a bearing is faulty or not, the controller comprising processing circuitry, the processing circuitry being configured to cause the controller to:
   obtain, as a measurement signal, metal particles counting data, where the metal particles counting data indicates number of metal particles present in lubrication oil of the bearing per time unit;
   differentiate the measurement signal, resulting in a differentiated measurement signal; and
   decide, depending on how large share of a probability density estimate of the differentiated measurement signal is above a threshold value, whether the bearing is faulty or not, wherein the probability density estimate of the differentiated measurement signal is represented by a histogram of the differentiated measurement signal.

4. The controller according to claim 3, wherein the threshold value corresponds to between 10 and 100 metal particles per day.

5. The controller according to claim 3, wherein said controller decides whether the bearing is faulty or not based on applying a statistical binary decision method to a parameter defined by the share of a probability density estimate of the differentiated measurement signal being above the threshold value.

6. The controller according to claim 3, wherein the time unit is one hour, one day, or one week.

7. The controller according to claim 3, wherein the bearing is a rolling-element bearing, and/or is part of an electric podded azimuth thruster.

8. The controller according to claim 3, wherein the controller is configured to:
apply a sliding window to the differentiated measurement signal, resulting in vectors of windowed differentiated measurement signals.

9. The controller according to claim 8, wherein the controller is configured to:
obtain one probability density estimate of the differentiated measurement signal per vector of the of windowed differentiated measurement signal,
wherein the decision by the controller is performed for each probability density estimate such that one decision whether the bearing is faulty or not is made per each probability density estimate.

10. The controller according to claim 3, wherein the histogram comprises bins ranging from a lowest-most bin to a highest-most bin, and wherein the share of the probability density estimate of the differentiated measurement signal to compare to the threshold value is defined by 1−r, where r has a value given by relative number of values of the differentiated measurement signal belonging to the lowest-most bin of the histogram.

11. The controller according to claim 10, wherein the histogram at least comprises a first bin representing smallest differentiated measurement signal and a last bin representing largest differentiated measurement signal, and wherein the share of the probability density estimate of the differentiated measurement signal to compare to the threshold value is defined by that share of the differentiated measurement signal being located in all but the first bin.

12. The controller according to claim 3, wherein the histogram at least comprises a first bin representing smallest differentiated measurement signal and a last bin representing largest differentiated measurement signal, and wherein the share of the probability density estimate of the differentiated measurement signal to compare to the threshold value is defined by that share of the differentiated measurement signal being located in all but the first bin.

13. The controller according to claim 12, wherein the histogram further comprises at least one middle bin, each at least one middle bin representing increasing differentiated measurement signal between the smallest differentiated measurement signal and the largest smallest differentiated measurement signal, and wherein the share of the probability density estimate of the differentiated measurement signal to compare to the threshold value is defined by that share of the differentiated measurement signal being located in all but the first bin.

14. The controller according to claim 3, wherein the measurement signal comprises K samples in total, wherein a sample k of the measurement signal is represented by $Fe[k]$, where $k=1, 2, \ldots, K$, and wherein the differentiated measurement signal, represented by $dFe[k]$, is given by:

$$dFe[k]=(Fe[k+1]-Fe[k])/(t[k+1]-t[k]), \text{ for } k=1,2,\ldots,K-1,$$

where $t[k]$ represents point in time for sample k.

15. The controller according to claim 14, wherein the probability density estimate of the differentiated measurement signal is represented by a histogram of the differentiated measurement signal.

16. The controller according to claim 14, wherein the threshold value corresponds to between 10 and 100 metal particles per day.

* * * * *